(12) United States Patent
Zhu

(10) Patent No.: US 10,321,864 B2
(45) Date of Patent: Jun. 18, 2019

(54) FILM FOR BIOSENSORS AND PREPARATION METHOD

(71) Applicant: MEDTRUM TECHNOLOGIES INC., Shanghai (CN)

(72) Inventor: Xiaoqing Zhu, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 545 days.

(21) Appl. No.: 14/906,505

(22) PCT Filed: Apr. 4, 2014

(86) PCT No.: PCT/CN2014/074773
§ 371 (c)(1),
(2) Date: Jan. 20, 2016

(87) PCT Pub. No.: WO2015/100868
PCT Pub. Date: Jul. 9, 2015

(65) Prior Publication Data
US 2016/0157765 A1 Jun. 9, 2016

(30) Foreign Application Priority Data
Jan. 2, 2014 (CN) .......................... 2014 1 0002608

(51) Int. Cl.
*A61B 5/1486* (2006.01)
*A61B 5/1468* (2006.01)
(Continued)

(52) U.S. Cl.
CPC ........ *A61B 5/14865* (2013.01); *A61B 5/1468* (2013.01); *A61B 5/1486* (2013.01);
(Continued)

(58) Field of Classification Search
CPC ............ A61B 5/14865; A61B 5/14532; A61B 2562/125; A61B 5/1468; A61B 5/1486;
(Continued)

(56) References Cited

U.S. PATENT DOCUMENTS 5,063,081 A * 11/1991 Cozzette ................ B01L 3/0268
204/403.1
5,200,051 A * 4/1993 Cozzette ................ B01L 3/0268
204/403.07
(Continued)

FOREIGN PATENT DOCUMENTS

CN 1576298 A 2/2005
CN 101253211 A 8/2008
(Continued)

OTHER PUBLICATIONS

European Search Report for 14876096.0, dated Nov. 24, 2016.
(Continued)

*Primary Examiner* — Navin Natnithithadha
(74) *Attorney, Agent, or Firm* — Yue (Robert) Xu; Apex Attorneys at Law, LLP

(57) ABSTRACT

The present invention relates to the field of film materials for biosensors, in particular to a film for biosensors and a preparation method. Provided is an organosilicon polymer, the raw materials thereof comprising the following components: at least one active organosilane, at least one curing agent, at least one optional hydrophilic copolymer and at least one optional regulator and/or filling. The membrane prepared from the provided organosilicon polymer has outstanding oxygen permeability and is adjustable in water absorption rate, and can put regulation and restriction on the diffusion of analytes (e.g. glucose) and interferents (e.g. acetaminophen). Meanwhile, the provided organosilicon polymer film also has indispensable physical strength and superior biocompatibility, and can serve as a multifunctional (Continued)

polymer film material for biosensors, such as anti-interference layer, analyte regulating layer and biocompatible layer.

17 Claims, 12 Drawing Sheets

(51) Int. Cl.
  *A61B 5/1473*  (2006.01)
  *C08G 18/73*  (2006.01)
  *C08G 18/61*  (2006.01)
  *C08L 83/08*  (2006.01)
  *C08L 83/12*  (2006.01)
  *C08L 83/04*  (2006.01)
  *C08G 77/12*  (2006.01)
  *C08G 77/20*  (2006.01)
  *C08G 77/26*  (2006.01)
  *C08G 77/46*  (2006.01)
  *C08G 18/50*  (2006.01)
  *A61B 5/145*  (2006.01)

(52) U.S. Cl.
  CPC ...... *A61B 5/14532* (2013.01); *C08G 18/5024* (2013.01); *C08G 18/61* (2013.01); *C08G 18/73* (2013.01); *C08L 83/04* (2013.01); *C08L 83/08* (2013.01); *C08L 83/12* (2013.01); *A61B 5/1473* (2013.01); *A61B 2562/125* (2013.01); *C08G 77/12* (2013.01); *C08G 77/20* (2013.01); *C08G 77/26* (2013.01); *C08G 77/46* (2013.01)

(58) Field of Classification Search
  CPC ............... A61B 5/1473; A61B 5/1495; C08G 18/5024; C08G 18/61; C08G 18/73; C08G 77/12; C08G 77/20; C08G 77/26; C08G 77/46; C08L 83/04; C08L 83/08; C08L 83/12

USPC .......................................... 600/309, 345–366
See application file for complete search history.

(56) References Cited

U.S. PATENT DOCUMENTS

| | | | | |
|---|---|---|---|---|
| 5,212,050 A * | 5/1993 | Mier | ..................... | B01L 3/0268 422/930 |
| 5,466,575 A * | 11/1995 | Cozzette | ............... | B01L 3/0268 204/403.1 |
| 5,554,339 A * | 9/1996 | Cozzette | ............... | B01L 3/0268 422/50 |
| 5,777,060 A * | 7/1998 | Van Antwerp | ..... | A61B 5/14865 528/28 |
| 5,786,439 A * | 7/1998 | Van Antwerp | ..... | A61B 5/14865 427/2.12 |
| 5,837,446 A * | 11/1998 | Cozzette | ............... | B01L 3/0268 435/6.11 |
| 5,837,454 A * | 11/1998 | Cozzette | ............... | B01L 3/0268 435/6.11 |
| 2002/0123087 A1* | 9/2002 | Vachon | ............. | C08G 18/5024 435/14 |
| 2006/0258761 A1* | 11/2006 | Boock | ................ | A61B 5/14532 521/50 |

FOREIGN PATENT DOCUMENTS

EP   0876604 A1  11/1998
WO  98/17995 A1  4/1998

OTHER PUBLICATIONS

International Search Report (in Chinese with English translation) for PCT/CN2014/074773, dated Sep. 29, 2014, ISA/CN.
Oxygen tension at the subcutaneous implantation site of glucose sensors. Fischer, A. Hidde, T. von Woedtke, K. Rebrin, and P. Abel, Biomed.Biochim.Acta.,1989, vol. 48, pp. 965-971.

* cited by examiner

R=Me; Et; Ph;Ar.
R' is a monovalent organic group, e.g., H, $C_yH_{2y+1}$, Ar
X=OH; $CH_2CH_2OH$; $OCH_2CH_2OH$; OMe; OEt; $CH_2CH_2NH_2$; $CH_2CH_2CH_2NH_2$; $CH_2CH_2CH_2COOH$; H.

diisocyanate glutaraldehyde

FILM FOR BIOSENSORS AND PREPARATION METHOD

CROSS-REFERENCE TO RELATED APPLICATIONS

The present application is a National Stage Application of International Application No. PCT/CN2014/074773, filed on Apr. 4, 2014, which claims priority to Chinese patent application No. 201410002608.8, filed on Jan. 2, 2014, and entitled "FILM FOR BIOSENSORS AND PREPARATION METHOD", the entire disclosure of which is incorporated herein by reference.

TECHNICAL FIELD

The present disclosure generally relates to the field of film materials for biosensors, and more particularly, to a film of a biosensor and a method for forming a film of a biosensor.

BACKGROUND

Biosensors are devices which can convert the concentration of a single chemical analyte in a complex system by using various biological materials (e.g., cells, enzymes, tissues) into detection signals (e.g., electricity, sound, light, heat) that can be analyzed and processed. Nowadays, various biosensors have been developed to analyze various analytes. Among the various biosensors, electrochemical enzyme biosensors which can convert the concentration of an analyte into an electrical signal by using enzymes gain the most attraction. The primary form of these electrochemical enzyme biosensors is amperometry glucose sensor which is of great significance to diabetics, especially in usage of continuous monitoring of blood glucose.

Nowadays, a lot of research work about implantable glucose biosensors has been conducted. Implantable glucose biosensors are used to monitor the glucose concentration of diabetics. In order to monitor the glucose concentration, an implantable glucose biosensor usually has an electrode coated with an enzyme. The enzyme used may be glucose oxidase (GOx). In the implantable glucose biosensor, the glucose oxidase reacts with glucose, which will produce a substance that can be detected by the electrode.

The principle reactions of the implantable glucose biosensor are as follows.

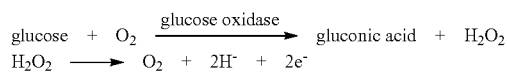

The critical factor of an enzyme biosensor with stableness and high sensitivity lies in that the output signal of the enzyme biosensor depends only on the analyte to be detected, and may not be influenced by the other substances and corresponding dynamic control factors (e.g., diffusion). The above recited reaction formulas clearly demonstrate the challenges that the implantable glucose biosensor is facing. In order to maximize the output current, the oxygen must be diffused as much as possible, so that volume of the oxygen on the reaction interface can be adequate. If there is no enough oxygen for the reaction of glucose oxidase and the glucose, the output current will be affected by the oxygen concentration rather than be proportional to glucose concentration. That is, in order to ensure the applicability of these kinds of glucose biosensors, glucose must be a limiting reagent. In other words, the oxygen concentration should be far more than the glucose concentration. It means necessary measures are required to increase the oxygen concentration and to reduce the glucose concentration. Or else, a biosensor without oxygen consumption is desired.

The main problem in the usage of glucose biosensors is that the ratio of the glucose concentration to the oxygen concentration in human bodies is opposite to the above recited optimum concentration condition for a biosensor. The glucose concentration in diabetics may range from 2 mM to 30 mM (36~540 mg/dL), and the typical oxygen concentration in tissues may range from 0.02 to 2 mM (Fischer, A. Hidde, H. vonWoedtke, K. Rebrin, and P. Abel, Biomed. Biochim. Acta. 1989, Vol. 48, pp. 965-971). The concentration ratio in diabetics will result in that the biosensor is not sensitive to minor changes in glucose concentration. The above recited main problem is generally called "oxygen starvation".

In the last decade, many approaches have been tried to solve the problem of oxygen starvation. The most simple and direct approach is to use a polymer film outside the biosensor. The polymer film has good oxygen permeability, and can regulate the permeance of glucose. The polymer film also has good physical stability and strength, certain adhesion, good biocompatibility and good compatibility with the enzyme used in biosensors. Based on this strategy, people have successfully manufactured a variety of homogeneous or heterogeneous polymer film materials, among which the most prominent material is organosilicone compound. Organosilicone compound is also the main material disclosed in the present disclosure.

In order to be used in vivo, these implantable glucose biosensors should be easy to install and remove, small in volume, safe, nontoxic, accurate, stable and sensitive. In order to meet the safety requirements, the materials of the implantable glucose biosensors must be nontoxic, indissoluble, indiffusible and good in biocompatibility. In order to be used in vivo for a long time, the materials of the implantable glucose biosensors must also be stable enough to maintain their shapes and performance after being soaked in the body fluid for a long time.

SUMMARY

Organosilicon is a kind of polymer which has a skeleton including alternately arranged silicon atoms and oxygen atoms, and various organic groups associated with the silicon atoms in the skeleton. Organosilicon copolymer is a kind of polymer which includes a main-chain unit that includes silicon atoms associated with various groups. Organosilicon and the organosilicon copolymer are widely used in rubber, adhesive, sealant, anti-sticking coating, anti-foaming agent, etc. Organosilicon materials have a good biocompatibility and a low risk of adverse biochemical reactions, so they are popular in medical industry and widely used in various kinds of medical devices.

However, organosilicon is a hydrophobic material, and it will seriously limit glucose and other water soluble molecules to pass through. Therefore, existing organosilicon materials are not convenient and reliable in applications of biosensors.

The present disclosure generally relates to the field of film material for biosensors, and more particularly, to an organosilicon polymer which can be used in a biocompatibility film system of a biosensor. The biosensor may be used for analyte detection in a human body, for example, for detecting the glucose concentration in the body fluid.

The organosilicon polymer film material has good oxygen permeability, an adjustable water absorption rate, and can be used to adjust the permeability of analyte (e.g., glucose) and interferent (e.g., acetaminophen). Besides, it has certain physical strength and a good biocompatibility, and can be used as a material for multifunctional polymer films of a biosensor. The organosilicon polymer includes: (a) an active organosilane with at least one terminal functional group such as hydroxyl, amino, carboxyl, hydrogen, alkoxyl, etc.; (b) a hydrophilic copolymer with at least one terminal functional group or at least one pendant functional group, which may be polyether, polyester or polycarbonate terminated with hydroxyl or amino, or polymer with amino; (c) a siloxane or non-siloxane curing agent, which may be siloxane, diisocyanate or glutaraldehyde, wherein the curing agent may be a chain extender with two degrees of functionality, or a cross-linking agent with three or more functional groups; (d) a property modifier or an reinforcing filler, which can be used to improve the physical properties and diffusion properties of a film to be formed with the organosilicon polymer, wherein the modifier may include short chain polydimethylsiloxane terminated with methyl, or some small molecules such as diol, triol and diamine, wherein the filler may include polytetrafluoroethylene nano particles, carbon-white or graphene.

According to one embodiment of the present disclosure, an organosilicon polymer is provided. The organosilicon polymer includes: at least one active organosilane, at least one curing agent, optionally at least one hydrophilic copolymer, and optionally at least one modifier, at least one filler, or a combination thereof, wherein the curing agent is selected from a chain extender with two degrees of functionality and a cross-linking agent with three or more functional groups.

In some embodiments, the organosilicon polymer includes: 100 parts by weight of the active organosilane, from 0 to 100 parts by weight of the hydrophilic copolymer, from 0 to 20 parts by weight of the modifier, from 0 to 10 parts by weight of the filler, and curing agent, wherein the active organosilane includes one or more functional groups;

wherein the hydrophilic copolymer is a hydrophilic polymer with one or more functional groups; and wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer; if the curing agent is a cross-linking agent, the number of moles of the curing agent is 1.05 to 1.20 times the sum of the number of moles of the functional groups of the active organosilane and the number of moles of the functional groups of the hydrophilic copolymer.

In some embodiments, the organosilicon polymer includes: 100 parts by weight of the active organosilane, from 0 to 75 (or 2 to 75) parts by weight of the hydrophilic copolymer, from 0 to 10 parts by weight of the modifier, from 0 to 5 parts by weight of the filler, and the curing agent, wherein the active organosilane includes one or more functional groups;

wherein the hydrophilic copolymer is a hydrophilic polymer with one or more functional groups; and wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer; if the curing agent is a cross-linking agent, the number of moles of the curing agent is 1.10 to 1.15 times the sum of the number of moles of the functional groups of the active organosilane and the number of moles of the functional groups of the hydrophilic copolymer.

The active organosilane selected in embodiments of the present disclosure is different from the conventional inactive organosilane. The active organosilane selected in the present disclosure has functional groups, for example, functional terminal groups, which may further participate in reactions. In some embodiments, the organosilicon polymer has a certain molecular weight range, and can conveniently form a biocompatibility film which has advantages like improved strength, toughness, tear resistance, stability and so on, and thus can be used in vivo.

In some embodiments, a main part of the active organosilane is polydimethylsiloxane (PDMS), wherein a part of methyl groups of the polydimethylsiloxane (PDMS) is substituted by monovalent organic groups, and the substitution rate is less than or equal to 30%. The monovalent organic groups are selected from hydrogen, aliphatic chain, aromatic chain, ether chain, or a combination thereof.

In some embodiments, the one or more functional groups of the active organosilane are selected from hydroxyl group, amino group, carboxyl group, hydrogen group, alkoxyl group, phenoxyl group, vinyl group, acyl group, oxime group, cyano group, allyl group, epoxy group, isocyano group, or a combination thereof.

In some embodiments, the one or more functional groups of the active organosilane are selected from hydroxyl group, amino group, or a combination thereof.

In some embodiments, the hydroxyl group is hydroxypropyl, the amino group is ethylamino or aminopropyl, the carboxyl group is butyric acid group, and the alkoxyl group is methoxyl or ethoxyl.

In some embodiments, the one or more functional groups of the hydrophilic copolymer are terminal functional groups or pendant functional groups, and the one or more functional groups of the hydrophilic copolymer are hydroxyl groups or amino groups.

In some embodiments, the hydrophilic copolymer is polyether, polyester, polycarbonate, polyamide, or other polymers with pendant hydroxyl or pendant amino.

In some embodiments, the hydrophilic copolymer is selected from one or more of polypeptides and proteins including polyethylene glycol terminated with amino, polypropylene glycol terminated with amino, poly(2-hydroxyethyl)methacrylate, polyallylamine, polylysine and gelatin.

In some embodiments, the curing agent is selected from molecules with two degrees of functionality (also called as chain extender), and three or more degrees of functionality (also called as cross-linking agent).

In some embodiments, the cross-linking agent is a silicane cross-linking agent that can participate in a condensation reaction and thus small molecules such as water, methanol, ethanol, acetone, acetic acid, etc, can be removed.

In some embodiments, the cross-linking agent is selected from trimethoxy(methyl)silane, trimethoxy(ethyl)silane, triethoxy(methyl)silane, triethoxy(ethyl)silane, tetraethoxysilane, methylsilanetriyl triacetate, aminopropyl trimethoxysilane, aminopropyl triethoxysilane, and bis[3-(triethoxysilyl) propyl]carbamide.

In some embodiments, the chain extender is a silicane chain extender, diisocyanate or glutaraldehyde.

In some embodiments, the silicane chain extender has terminal vinyl which may react with PDMS terminated with hydrogen, for example, the silicane chain extender may be polydimethylsiloxane terminated with vinyl.

In some embodiments, the diisocyanate is selected from small molecules and high molecules with aliphatic chain, aliphatic cyclic, aromatic nucleus or multiple rings.

In some embodiments, the diisocyanate is selected from 1,6-hexamethylene diisocyanate, diisocyanate with a structure of isophorone, 1,3-phenyl diisocyanate and other aromatic diisocyanate.

In some embodiments, the number of moles of the curing agent is determined by the number of moles of functional groups which can participate in reactions. For chain extension reactions, the number of moles of the curing agent is equivalent to the number of moles of the functional groups which participate in the reactions. For cross-linking reactions, the number of moles of the curing agent is more than the number of moles of the functional groups, the number of moles of the curing agent is 1.05 to 1.20 times the number of moles of the functional groups. Furthermore, the number of moles of the curing agent is 1.10 to 1.15 times the number of moles of the functional groups.

In some embodiments, the modifier and the filler are used to regulate particular properties of the organosilane material.

In some embodiments, the modifier is selected from inactive silicane and active small molecules, for example, selected form short chain PDMS terminated with methyl, aliphatic diol, aliphatic triol, aliphatic diamine, aromatic diamine, or a combination thereof.

As is known to all, in the field of silica gel, suitable fillers can improve physical properties and diffusive properties of silica gel layers.

In some embodiments, the filler may be selected from but not limited to, fumed silica, aluminum oxide, carbon black, titanium dioxide, glass fiber, carbon fibre, diatomaceous earth, synthetic fibre (e.g., nylon, polyethylene terephthalates, polyving alcohol, polyvinyl chloride, acrylonitrile), nano particle (e.g., polytetrafluoroethylene nano particle, silicon dioxide nano particle, graphene), etc. Hereunder is an example of graphene. When graphene is used in an anti-interference layer and an analyte regulation layer of a biosensor of the present disclosure, it may evidently improve physical properties of corresponding layers. When graphene is used in an enzyme layer of the biosensor, it may improve the activity and affinity of the enzyme. When graphene is used on a surface of a conducting layer of the biosensor, it may increase the area of the effective conductive interface and improve the affinity of two adjacent layers.

According to one embodiment of the present disclosure, a method for forming the above described organosilicon polymer is provided. The method includes copolymerization or cross-linking curing of the active organosilane, wherein the active organosilane is modified by a treatment such as chain extension, cross-linking, etc.

According to one embodiment of the present disclosure, an application of the above described organosilicon polymer in the field of biosensor manufacturing is provided.

In some embodiments, a film of a biosensor is provided. The film of the biosensor is formed by the above described organosilicon polymer by using spin coating, dip coating, spray coating, or inkjet printing.

Experiments show that the polymer film of the present disclosure has good oxygen permeability and an adjustable water absorption rate, thus can adjust and limit the diffusion of the analyte (e.g., glucose) and the interferent (e.g., acetaminophen). Besides, the polymer film has an adequate physical strength and good biocompatibility, and can be used as a material for multifunctional polymer films of biosensors. For example, it can be used as a material for an anti-interference layer, an analyte regulation layer, and a biocompatibility layer.

According to one embodiment of the present disclosure, an implantable biosensor is provided. The biosensor includes an electrical conducting layer which has three electrodes. The electrical conducting layer is covered by the following function layers from inside to outside: an anti-interference layer, an enzyme layer, an analyte regulation layer and a biocompatibility layer. The function layers are formed by the organosilicon polymer.

In some embodiments, the function layers are formed by using spin coating, dip coating, spray coating, or inkjet printing.

In some embodiments, the anti-interference layer is formed by the organosilicon polymer, and the organosilicon polymer includes: 100 parts by weight of active organosilane, from 0 to 15 (preferably 1 to 10, more preferably 2 to 7) parts by weight of hydrophilic copolymer, from 0 to 10 parts by weight of modifier, from 0 to 5 parts by weight of filler, and curing agent, wherein the active organosilane includes one or more functional groups;

wherein the hydrophilic copolymer is a hydrophilic polymer with one or more functional groups, which may be selected from polyethylene glycol (PEG), poly(2-hydroxyethyl)methacrylate and polylysine; and wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer, if the curing agent is a cross-linking agent, the number of moles of the curing agent is 1.1 to 1.15 times the sum of the number of moles of the functional groups of the active organosilane and the number of moles of the functional groups of the hydrophilic copolymer.

In some embodiments, a thickness of the anti-interference layer ranges from 0.1 to 10 micron, and preferably ranges from 0.5 to 5 micron.

In some embodiments, the regulation layer is formed by the organosilicon polymer, and the organosilicon polymer includes: 100 parts by weight of active organosilane, from 0 to 25 (preferably 2 to 20, more preferably 5 to 15) parts by weight of hydrophilic copolymer, from 0 to 10 parts by weight of modifier, from 0 to 5 parts by weight of filler, and curing agent, wherein the active organosilane includes one or more functional groups;

wherein the hydrophilic copolymer is a hydrophilic polymer with one or more functional groups, which may be selected from copolymerized and grafted polyethylene glycol (PEG), or selected from but not limited to other diol substances such as polypropylene glycol, polyester, polyamide and polycarbonate; and wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer, if the curing agent is a cross-linking agent, the number of moles of the curing agent is 1.1 to 1.15 times the sum of the number of moles of the functional groups of the active organosilane and the number of moles of the functional groups of the hydrophilic copolymer.

In some embodiments, a thickness of the regulation layer ranges from 1 to 50 micron, and preferably ranges from 5 to 15 micron.

In some embodiments, the biocompatibility layer is formed by the organosilicon polymer, and the organosilicon polymer includes: 100 parts by weight of active organosilane, from 5 to 100 (preferably 10 to 80, more preferably 25 to 75) parts by weight of hydrophilic copolymer, from 0 to 10 parts by weight of modifier, from 0 to 5 parts by weight of filler, and curing agent, wherein the active organosilane includes one or more functional groups;

wherein the hydrophilic copolymer is a hydrophilic polymer with one or more functional groups, which may be selected from copolymerized and grafted polyethylene glycol (PEG), or selected from but not limited to other diol substances such as polypropylene glycol, polyester, polyamide and polycarbonate; and wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer, if the curing agent is a cross-linking agent, the number of moles of the curing agent is 1.1 to 1.15 times the sum of the number of moles of the functional groups of the active organosilane and the number of moles of the functional groups of the hydrophilic copolymer.

In some embodiments, a thickness of the biocompatibility layer ranges from 5 to 100 micron, and preferably ranges from 10 to 30 micron.

In some embodiments, the three electrodes of the biosensor are a working electrode, a reference electrode and a counter electrode.

In some embodiments, the reference electrode is an Ag/AgCl electrode.

In some embodiments, the counter electrode is a platinum electrode.

In some embodiments, the working electrode is a platinum electrode.

Coating the film of the biosensor is implemented by using a commercial rotary coating device. The rotation rate ranges from 1000 to 5000 rpm, which is adjusted based on a stickiness of the polymer solution and a required thickness of the film. Coating the film of the biosensor can also use other common film formations methods in the field, for example, dip coating, spray coating, and inkjet printing.

BRIEF DESCRIPTION OF THE DRAWINGS

FIG. 12a is a schematic top view which illustrates distribution of electrodes on a substrate of the glucose biosensor sensor;

FIG. 12b is a schematic side view which illustrates distribution of the electrodes on the substrate of the glucose biosensor sensor from another direction;

FIG. 12c is a cross-sectional view of a working electrode of the glucose biosensor, which illustrates functional layers on the working electrode, the functional layers including an anti-interference layer, an enzyme layer, a regulation layer and a biocompatibility layer;

FIG. 13a schematically illustrates a relation of a glucose concentration and a response current of a glucose biosensor coated with an enzyme layer; and FIG. 13b schematically illustrates a relation of a glucose concentration and a response current of a glucose biosensor coated with an enzyme layer and regulation layer.

DETAILED DESCRIPTION

Figure 1:
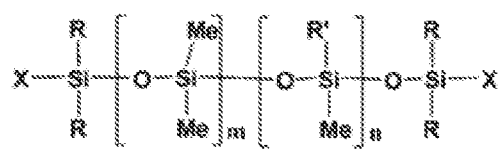
FIG. 1 schematically illustrates active siloxane polymers that can be used as a basic polymer in a polymerization reaction of the present disclosure.
Figure 1:
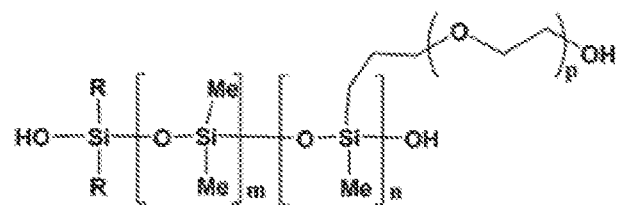

In order to clarify the objects, characteristics and advantages of the present disclosure, embodiments of the present disclosure will be described in detail in conjunction with the accompanying drawings. The disclosure will be described with reference to certain embodiments. Accordingly, the present disclosure is not limited to the embodiments disclosed. It will be understood by those skilled in the art that various changes may be made without departing from the spirit or scope of the disclosure.

It will be understood that all processing equipment and devices are routine equipment and devices in the art, and the pressure values and ranges referred to herein are absolute pressures, unless specifically stated otherwise.

In addition, it is noted that the one or more method steps mentioned herein do not preclude the presence of additional method steps before or after the combination of the recited steps or intervening method steps between those steps expressly identified, unless specifically stated otherwise. It is also noted that the connecting relation of one or more equipment or devices does not preclude the presence of additional equipment or devices before or after the combination of the recited equipment or devices, or intervening equipment or devices between those equipment or devices expressly identified, unless specifically stated otherwise. Moreover, unless specifically stated otherwise, the serial numbers of processing steps are merely for identifying these processing steps, but not intending to limit the order of the processing steps or the scope of embodiments. Any adjustment or modification of the sequence, without substantially changing the technical solution, shall be in the scope of the present disclosure.

Active Organosilane

Active organosilane polymer selected in embodiments of the present disclosure is different from the conventional inactive organosilane. The polymer has one or more functional groups, for example, functional terminal groups, which can further participate in reactions. In some embodiments, the polymer has a certain molecular weight range, and can conveniently form a cross-linking biocompatibility film which has advantages like improved strength, toughness, tear resistance, stability and so on, and thus can be used in vivo.

In some embodiments, a main part of the active organosilane is polydimethylsiloxane (PDMS). In some embodiments, a part of methyl groups of the polydimethylsiloxane (PDMS) is substituted by monovalent organic groups, for example, hydrogen, aliphatic chain, aromatic chain, ether chain, etc.

In some embodiments, the functional groups of the active organosilane are selected from hydroxyl group, amino group, carboxyl group, hydrogen group, alkoxyl group, phenoxyl group, vinyl group, acyl group, oxime group, cyano group, allyl group, epoxy group and isocyano group, or a combination thereof, most preferably, selected from hydroxyl group and amino group. Specifically, the hydroxyl group is hydroxypropyl, the amino group is ethylamino or aminopropyl, the carboxyl group is butyric acid group, and the alkoxyl group is methoxyl, ethoxyl, etc.

FIG. 1 schematically illustrates some embodiments of an active organosilane according to the present disclosure.

Hydrophilic Copolymer

In some embodiments, the hydrophilic copolymer is a polymer with at least one terminal functional group or at least one pendant functional group, wherein the functional group is selected from hydroxyl group and amino group.

In some embodiments, the active functional group of the hydrophilic copolymer may be hydroxyl group and amino group.

Specifically, in some embodiments, the hydrophilic copolymer is selected from polyether, polyester, polycarbonate, polyamide, and other polymers with at least one pendant hydroxyl group or at least one pendant amino group.

Figure 2:
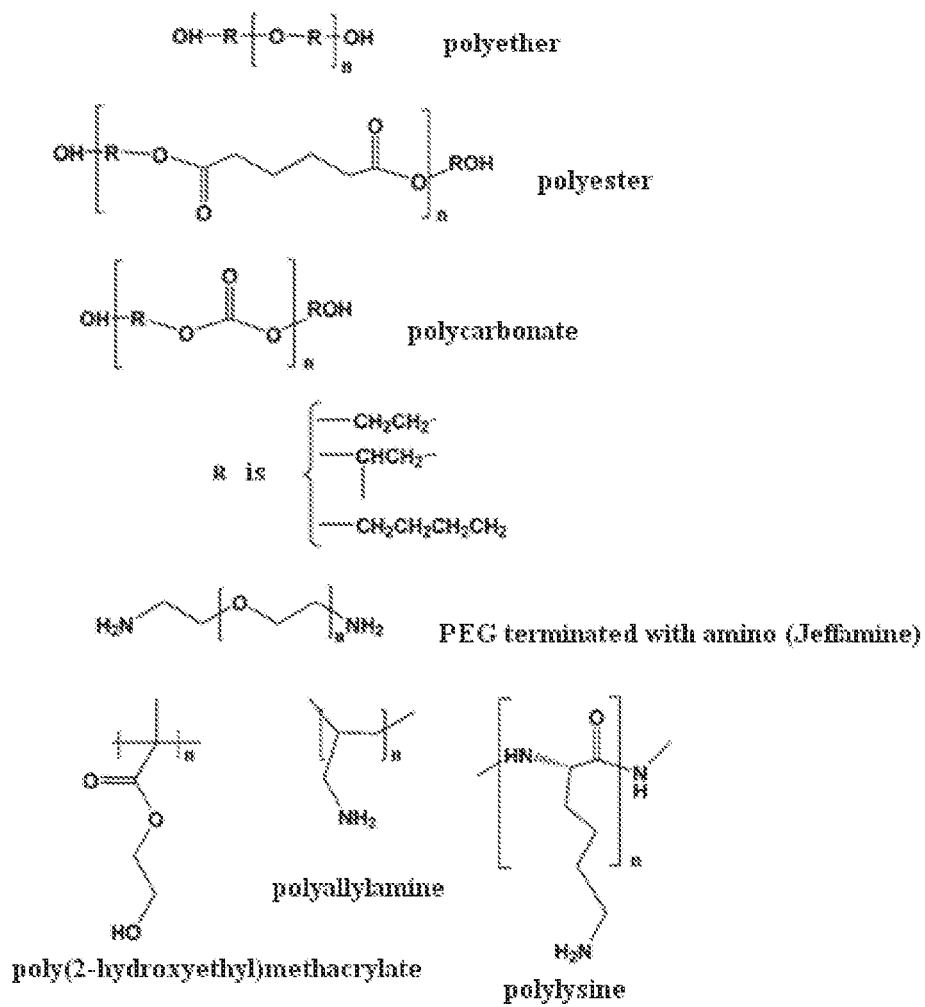
FIG. 2 schematically illustrates active non-siloxane polymers that can be used as a copolymer in a polymerization reaction of the present disclosure.

FIG. 2 schematically illustrates some embodiments of the hydrophilic copolymer according to the present disclosure.

In some embodiments, the amount of the hydrophilic copolymer in the present disclosure is from 0 to 100 parts by weight (based on a condition that the amount of the active organosilane is 100 parts by weight), preferably, from 2 to 75 parts.

Curing Agent

In some embodiments, the curing agent is selected from molecules with two degrees of functionality (also called as chain extender), and three or more degrees of functionality (also called as cross-linking agent).

In some embodiments, the cross-linking agent includes silicane. A silicane cross-linking agent can participate in a condensation reaction and thus small molecules such as water, methanol, ethanol, acetone, acetic acid, etc, can be removed.

In some embodiments, the chain extender is selected from a silicane chain extender, diisocyanate and glutaraldehyde.

Specifically, in some embodiments, the silicane chain extender has terminal vinyl which may react with PDMS terminated with hydrogen.

Specifically, in some embodiments, the diisocyanate is selected from small molecules and high molecules with aliphatic chain, aliphatic cyclic, aromatic nucleus or multiple rings, preferably, selected from 1,6-hexamethylene diisocyanate, diisocyanate with a structure of isophorone, 1,3-phenyl diisocyanate and other aromatic diisocyanate.

Figure 3:
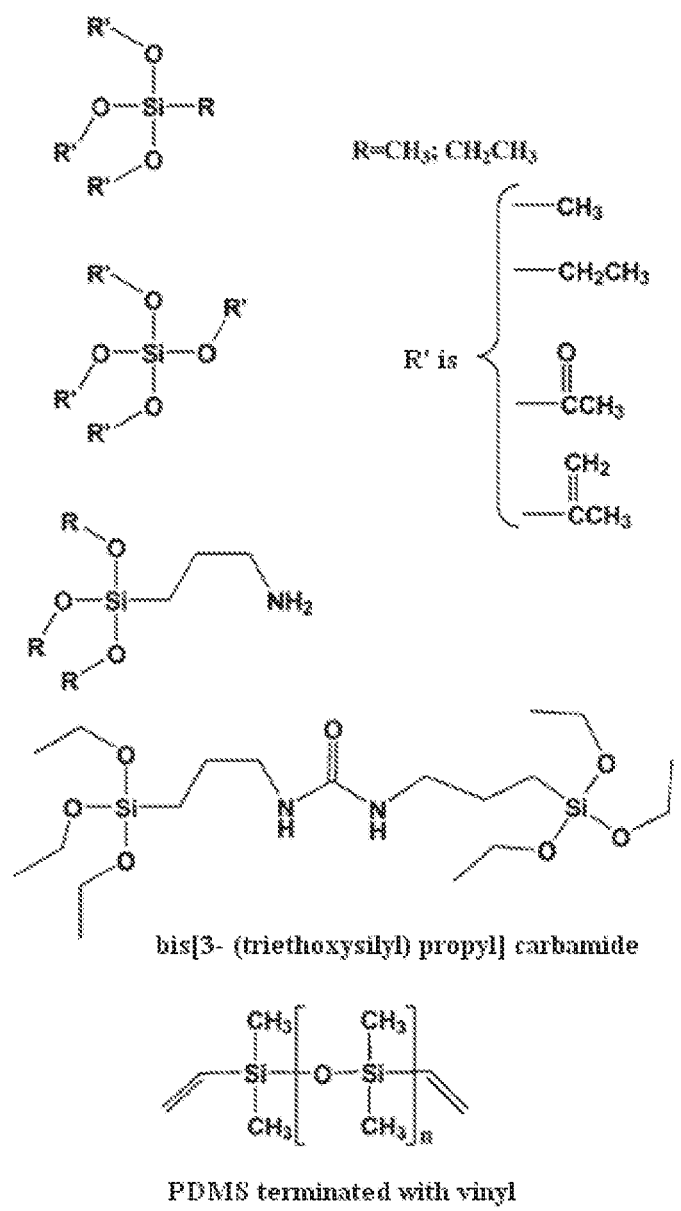
FIG. 3 schematically illustrates siloxanes that can be used as a curing agent in a polymerization reaction of the present disclosure.
Figure 4:
FIG. 4 schematically illustrates a diisocyanate and a glutaraldehyde that can be used as a curing agent in a polymerization reaction of the present disclosure.
Figure 4:
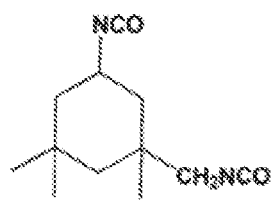
Figure 4:
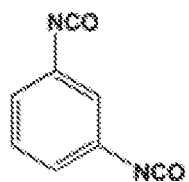
Figure 4:
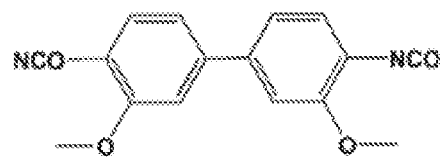
Figure 4:

FIG. 3 schematically illustrates some embodiments of the silicane curing agent according to the present disclosure. FIG. 4 schematically illustrates some embodiments of the non-silicane curing agent according to the present disclosure.

In some embodiments, the number of moles of the curing agent is determined by the number of moles of functional groups which can react in the reaction system. For chain extension reactions, the number of moles of the curing agent is equivalent to the number of moles of the functional groups which can react in the reaction system. For cross-linking reactions, the number of moles of the curing agent is more than the number of moles of the functional groups which can react in the reaction system. In some embodiments, the number of moles of the curing agent is 1.05 to 1.20 times the number of moles of the functional groups. Furthermore, the number of moles of the curing agent is 1.10 to 1.15 times the number of moles of the functional groups.

Modifier and Filler

In some embodiments of the present disclosure, the modifier and the filler are used to regulate particular properties of the organosilane material.

In some embodiments, the modifier is selected from inactive silicane such as short chain PDMS terminated with methyl, an active small molecule such as aliphatic diol, aliphatic triol, aliphatic diamine, aromatic diamine, or a combination thereof.

Figure 5:
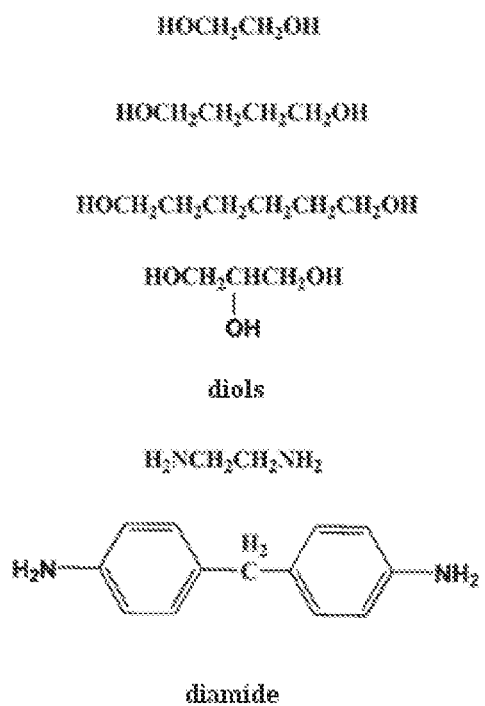
FIG. 5 schematically illustrates a short chain diol, a triol and a diamine that can be used as an active property modifier in a polymerization reaction of the present disclosure.
Figure 6:
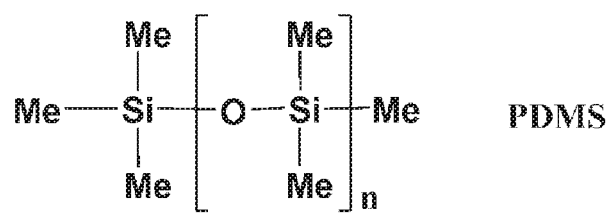
FIG. 6 schematically illustrates a short chain polydimethylsiloxane (PDMS) terminated with methyl that can be used as a non active property modifier in a polymerization reaction of the present disclosure.

FIG. 5 and FIG. 6 schematically illustrate some embodiments of the modifier according to the present disclosure.

In some embodiments, the amount of the modifier in the present disclosure is from 0 to 10 parts by weight (based on a condition that the amount of the active organosilane is 100 parts by weight), preferably, from 1 to 7.5 parts.

As is known to all, in the field of silica gel, suitable fillers can improve physical properties and diffusive properties of silica gel layers. In some embodiments, the filler may be selected from but not limited to, fumed silica, aluminum oxide, carbon black, titanium dioxide, glass fiber, carbon fibre, diatomaceous earth, synthetic fibre (e.g., nylon, polyethylene terephthalates, polyving alcohol, polyvinyl chloride, acrylonitrile), nano particle (e.g., polytetrafluoroethylene nano particle, silicon dioxide nano particle, graphene), etc. Hereunder is an example of graphene. When graphene is used in an anti-interference layer and an analyte regulation layer of a biosensor of the present disclosure, it may evidently improve physical properties of corresponding layers. When graphene is used in an enzyme layer of the biosensor, it may improve the activity and affinity of the enzyme. When graphene is used on a surface of a conducting layer of the biosensor, it may increase the area of the effective conductive interface and improve the affinity of two adjacent layers.

In some embodiments, the amount of the filler in the present disclosure is from 0 to 10 parts by weight (based on a condition that the amount of the active organosilane is 100 parts by weight), preferably, from 0.5 to 5 parts.

Reaction

In some embodiments, the organosilicon polymer is formed by at least one active organosilane, at least one curing agent, optionally at least one hydrophilic copolymer, and optionally at least one modifier and filler. Reaction conditions mainly depend on the curing agent used in polymerization, and are affected by catalysts and solvents that may be used in the polymerization.

Chain Extension Reaction and Functional Modification

Figure 7:
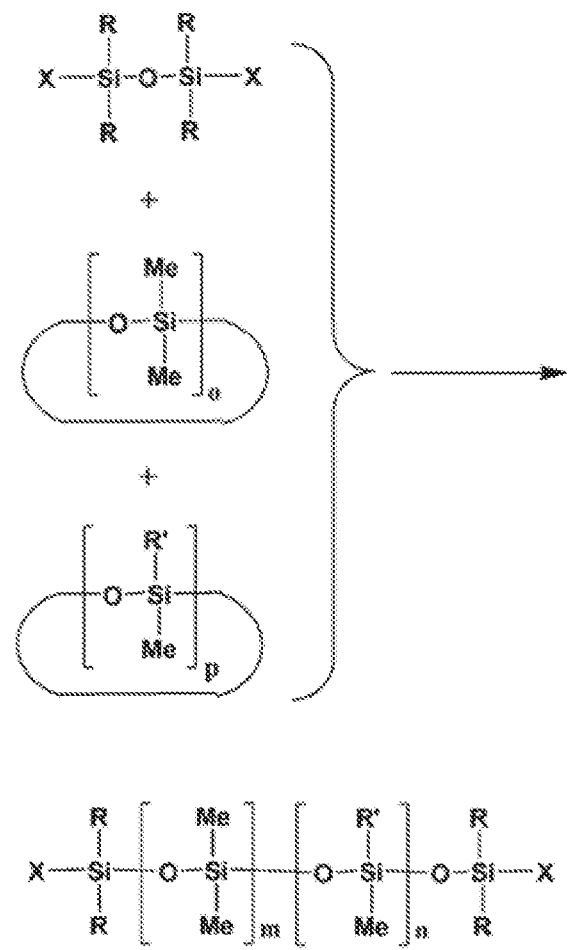
FIG. 7 schematically illustrates a chain extending reaction of an active PDMS.

People familiar with organosilane materials are clear that a simple organosilicon polymer can be subject to chain extension and functional modification by a ring opening polymerization. FIG. 7 schematically illustrates a chain extension reaction of an active organosilane. The polymerization uses a linear siloxane monomer and two ringed siloxane monomers. The terminal X of the linear siloxane monomer is an active group, which may be a hydroxyl group, an amino group, a carboxyl group, a hydrogen group, an alkoxyl group, etc. At least one ringed siloxane monomer is substituted by a monovalent organic group such as a hydrogen atom, an aliphatic chain, an aromatic chain, an ether chain, etc. Preferably, the monovalent organic group R' is a hydrophilic group. The monomer with hydrophilic group may be polymerized by itself, or polymerized with the ringed siloxane monomer, and then produces an irregular organosilicone copolymer or a block organosilicone copolymer. As the purification of the ringed siloxane monomer with hydrophilic group is easy, this method can effectively improve the degree of polymerization of organosilane. In order to clarify the chain extension reaction by those skilled in the art, an example 1 is provided later.

As is known to in the field of manufacturing organic silicon materials, the basic principles of the ring opening polymerizations are similar, and the ring opening polymerizations may produce polymers with various terminal functional groups or pendant functional groups. The polymers with hydrophilic terminal functional groups or pendant functional groups may be used as an elastic body, an adhesion agent or a sealant, and be further cross-linked.

Copolymerization

In some embodiments, the organosilicon polymer may polymerize with other polymers with two degrees of functionality, and then produce linear copolymers.

A copolymer usually is formed by three or more individual units. A basic unit for connecting these units may be diisocyanate. FIG. 4 schematically illustrates some embodiments of the diisocyanate. The copolymer also includes at least two other units that are used to form the main body of the desired copolymer. One unit is the organosilane which has good oxygen permeability. However, because common siloxanes do not have water permeability, they do not allow any glucose to pass through. In some embodiments, the organosilane is a polydimethylsiloxane with an active terminal group. FIG. 1 schematically illustrates some embodiments of polydimethylsiloxane with an active terminal group. Another unit is a hydrophilic polymer with a long chain, whose function is to regulate and control the water permeability of the desired copolymer. FIG. 2 schematically illustrates some embodiments of hydrophilic polymers used in the film for the biosensor. The hydrophilic polymers include diol, for example, polyethylene glycol (PEG), polypropylene glycol (PPG), and the same type diamine. Of course, as is known to those skilled in the art, they can be replaced by other diol or diamine.

When the copolymer is being formed, sometimes some modifiers (e.g., short chain diol or diamine) need to be added to improve the physical strength of the polymer, and to avoid affecting the glucose permeability of the polymer. In these cases, the modifiers illustrated in FIG. 5 and FIG. 6 have been used. FIG. 5 and FIG. 6 schematically illustrate some embodiments of the modifier according to the present disclosure.

The copolymerization may be bulk polymerization or solution polymerization. When solution polymerization is used, dimethylformamide (DMF) or tetrahydrofuran (THF) can be selected as a solvent. When the copolymerization is happening, the number of moles of the groups in the diisocyanate must be the same as the sum of the number of moles of the amino groups and the number of moles of the hydroxyl groups.

As water can react with diisocyanate, and then produce some undesired short chain polymers, necessary measures shall be taken to ensure that all solvents, reaction reagents and containers are as dry as possible. Short chain or long chain diol, and long chain diamine may be dried by azeotropic distillation with toluene. The solvents may be added to calcium hydride or molecular sieve, and then dried by distillation. The diisocyanate and the polysiloxane may be used directly or stored by adding molecular sieve.

Figure 8:
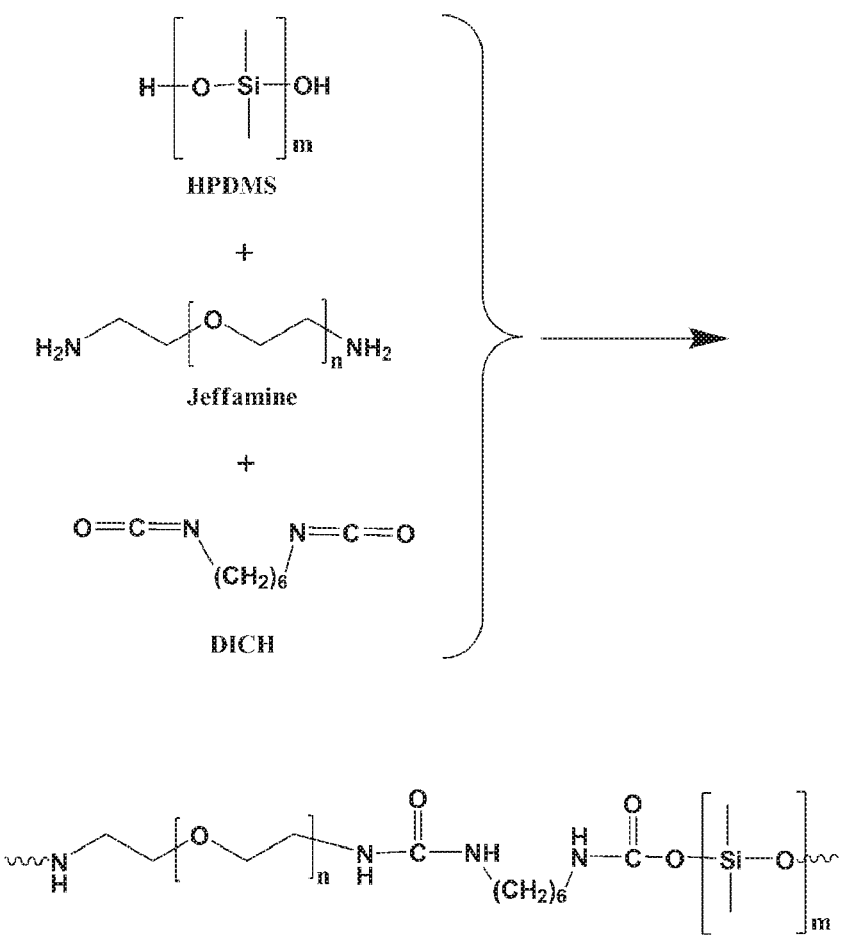
FIG. 8 schematically illustrates a polymerization of a Jeffamine, a diisocyanate and a PDMS terminated with hydroxyl, products of which include a carbamate chain unit and a carbamide chain unit.
Figure 9:
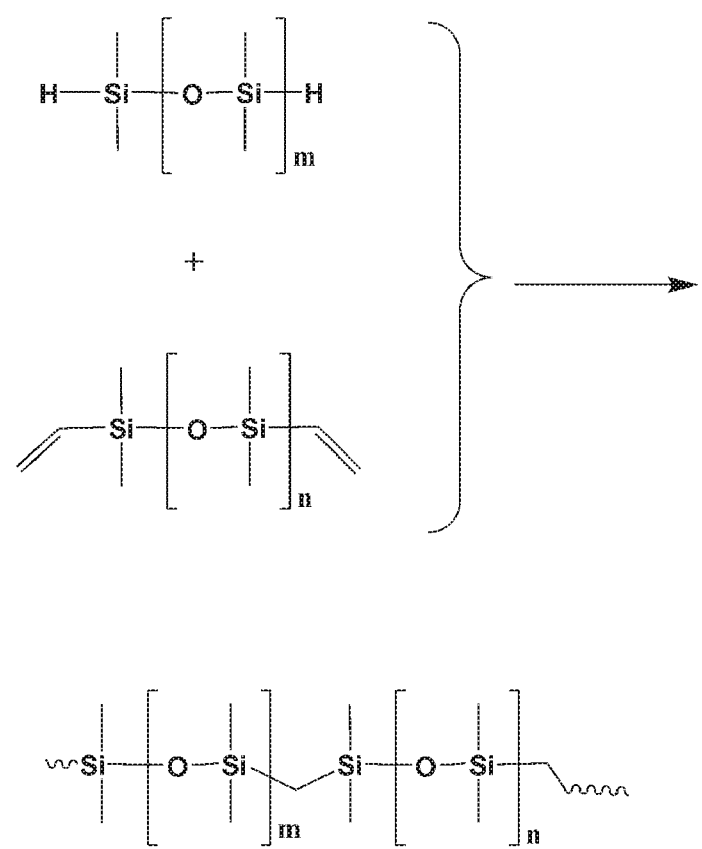
FIG. 9 schematically illustrates a polymerization reaction of a PDMS terminated with hydrogen and a siloxane curing agent with vinyl.

FIG. 8 and FIG. 9 schematically illustrate embodiments of two kinds of copolymerization reactions according to the present disclosure. FIG. 8 illustrates that polyetheramine (polyethylene glycol terminated with amino), PDMS terminated with hydroxyl (HPDMS) and diisocyanate react, and then produce products including amido bond and urea bond. In some embodiments, copolymerization may be carried out at 70 degree Celsius, and with an appropriate catalyst, for example, trace amounts of organotin. In order to clarify the copolymerization to those skilled in the art, an example 2 is provided later. FIG. 9 illustrates the copolymerization between PDMS terminated with hydrogen and polysiloxane terminated with vinyl. In some embodiments, copolymerization may be carried out at 75 degree Celsius, and with an appropriate catalyst, for example, Pt complex. In order to clarify the copolymerization to those skilled in the art, an example 4 is provided later.

Curing by Cross-Linking

Figure 10:
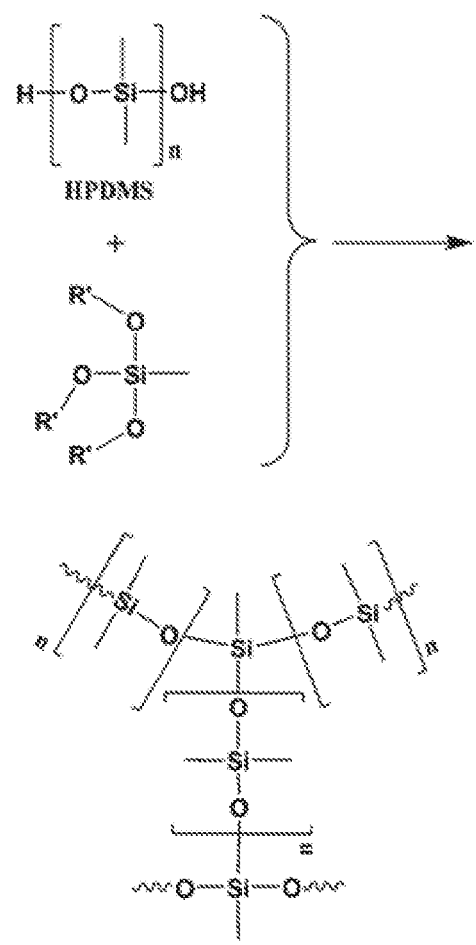
FIG. 10 schematically illustrates a condensation reaction of a PDMS terminated with hydroxyl and a siloxane curing agent with three functional groups.
Figure 11:
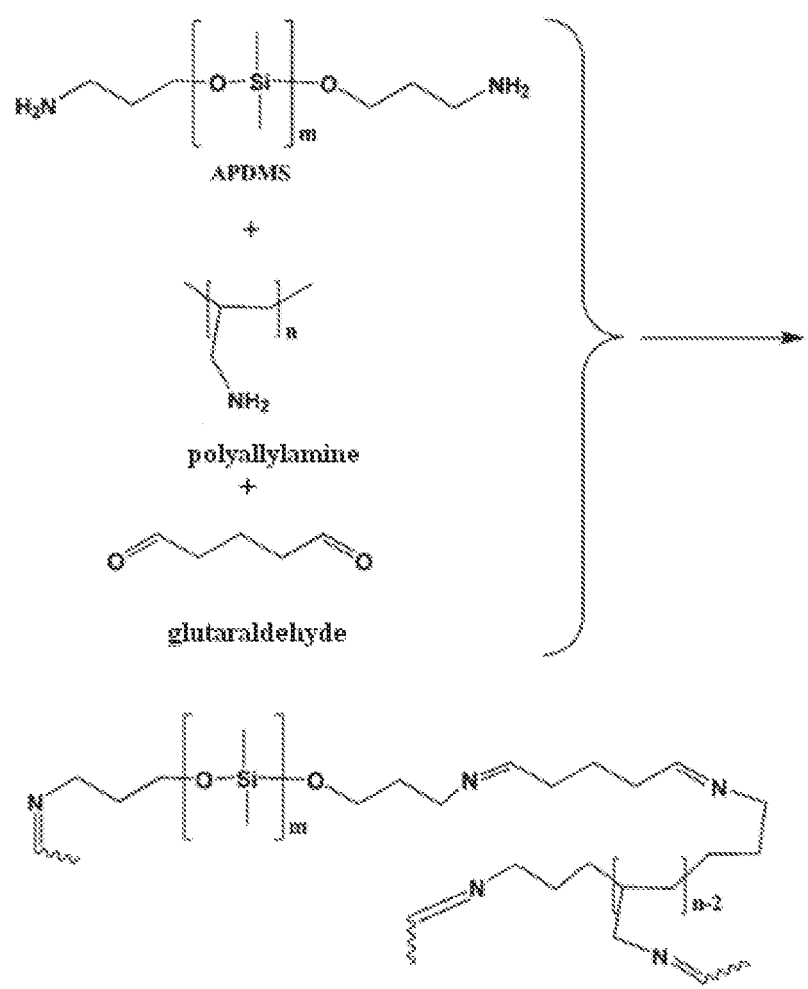
FIG. 11 schematically illustrates a polymerization reaction of a polyacryl ethylamine, a glutaraldehyde and a PDMS terminated with amino.

In some embodiments, the organosilicon polymer may be cured into a network polymer by using a cross-linking agent. FIG. 10 and FIG. 11 respectively schematically illustrate embodiments of two kinds of curing agent, a silicane curing agent and a non-silicane curing agent.

FIG. 10 illustrates the condensation reaction between polydimethylsiloxane (PDMS) terminated with hydroxy and a polysiloxane curing agent with three degrees of functionality according to one embodiment of the present disclosure. The curing process can be carried out at room temperature, and use an appropriate catalyst, for example, tetrabutyl titanate. The curing process mainly includes two stages: firstly, the siloxane curing agent is hydrolyzed, and then produces active silicon hydroxyl; secondly, the active silicon hydroxyl in the curing agent reacts (condensation) with the silicon hydroxyl in the base chain, and produces a polymer with Si—O—Si backbones. As water is an essential evocating agent, the hydrolysis of the siloxane curing agent only occurs in a moist environment, and the process is usually accompanied by removal of small molecules such as methanol, ethanol, acetone, acetic acid, etc. In order to clarify the copolymerization to those skilled in the art, an example 3 is provided later.

FIG. 11 illustrates the condensation reaction between PDMS terminated with amino and polyallylamine by using glutaraldehyde as a curing agent according to one embodiment of the present disclosure. As amino and aldehyde is very likely to react, the condensation reaction may be carried out at 30 degrees Celsius to 40 degrees Celsius without any catalyst. In order to clarify the copolymerization to those skilled in the art, example 5 is provided.

Manufacturing and Performance Testing of a Polymer Film

In some embodiments, the polymer film is formed by the following method. The method includes: mixing one or more active organosilane, optionally hydrophilic copolymer, and optionally one or more filler at a certain temperature; adding one or more curing agent and modifier, and optionally a catalyst to the mixture obtained in the last step; diluting the mixture obtained in the last step to an appropriate concentration (e.g., the solid content can range from 0.5% to 1%, 2%, 3%, 4%, 5%, 6%, 7%, 8%, 9%, 10%, 15%, 20%, 25%, 30%, 35%, 40%, 45%, 50%, 60%, 70%, 75%, or even higher) by using an appropriate solvent (e.g., toluene, THF, dichloromethane); coating the diluted mixture, using a device, for example, a wiped-film device, onto a non-cohesive substrate to form a polymer film, wherein the substrate may be glass, a silicon chip, a polyethene chip, or a polytetrafluoroethylene chip; heating and curing the polymer film; pulling the polymer film off from the substrate, when the polymer film is cured enough. The thickness of the polymer film can be measured by a device such as micro-calliper, etc. Another method may also be used to form the polymer film. For example, the method may include casting the diluted mixture onto a filter membrane with a known thickness. Assuming the diluted mixture fully fills the gap of the filter membrane, the thickness of the polymer film is the same as the thickness of the filter membrane. Other methods in common use in the art may also be used to form the polymer film, for example, solid extrusion, calendaring, thermal forming, extrusion and transfer forming, injection molding, spin coating, dip coating, and so on.

Diffusion Constant

Diffusion constant may be measured based on Fick's first law of diffusion in a standard diffusion cell, using the following formula:

$$J=-D\, dC/dx,$$

J is the diffusion flux, D is the diffusion constant of the target analyte, and $dC/dx$ is the concentration gradient of the target analyte in the diffuser film. The value of D depends on the nature of the analyte and properties of materials of the film, and D is a core parameter in the evaluating system. The minus in the formula represents that diffusion is towards the low concentration region. If conservation of mass is considered, Fick's second law will be used, and the following formula can be used: $dc/dt = D\, d^2C/dx^2$.

Water Absorption

Water absorption may be measured by a weighing method. A formula used is as follows:

$$\% \text{ Pickup} = (W_w - W_d)/W_d * 100\%,$$

wherein $W_w$ is a weight of the wet film after water absorption, $W_d$ is a weight of the dry film before water absorption.

Biosensor

Further, the present disclosure provides an implantable biosensor that may be used to monitor a target analyte such as glucose. The volume of the implantable glucose biosensor is small, so it can be easily implanted into the subcutaneous tissue of mammals, and used to real-timely and continuously monitor the glucose level.

Figure 12A:
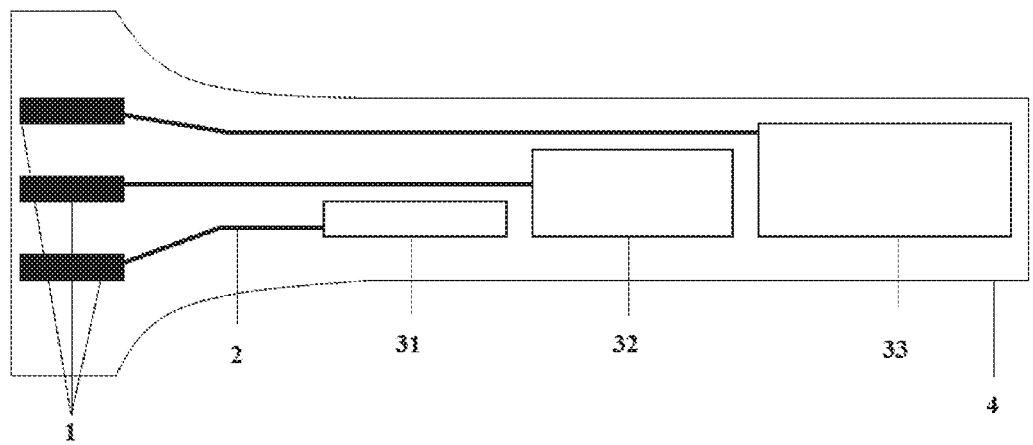
FIGS. 12a to 12c schematically illustrate a schematic structure of a glucose biosensor according to one embodiment.
Figure 12B:
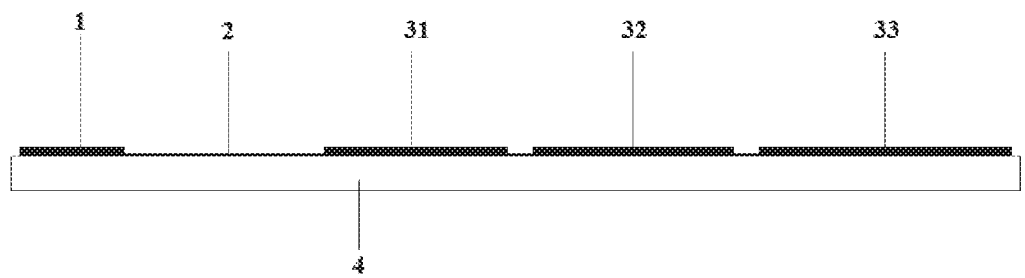

FIG. 12 schematically illustrates the structure of a glucose biosensor according to one embodiment of the present disclosure. The biosensor includes an electrical conducting layer including three electrodes which are a working electrode, a reference electrode and a counter electrode. Size and shape of the three electrodes may be the same or different. The electrodes are located on an insulated substrate, and may be arranged in parallel to arrange a gap between each two electrodes and avoid electrode connection. FIG. 12a and FIG. 12b respectively illustrates the distribution of electrodes (3) of the glucose biosensor on a substrate (4). The biosensor includes three electrodes (31, 32, 33) respectively connected to three pads (1) through wires (2). Specifically, the three electrodes are respectively a reference electrode (31), a counter electrode (32) and a working electrode (33). In some embodiments, the reference electrode is an Ag/AgCl electrode, and the counter electrode and the working electrode are platinum electrodes.

For the glucose biosensor, glucolase is usually located on the surface of the working electrode. The most commonly used enzyme is glucose oxidase which can react with glucose and produce a product which can be detected by the working electrode. The glucose oxidase may be cross-linked to structural protein (e.g., human serum albumin, bovine serum albumin) to form an enzyme layer, and the conditions of cross-linking is similar to example 5. The enzyme layer formed by the above method is stable, and can be used in vivo for a long time.

In order to protect the electrode and the enzyme layer, eliminate the interference signal, and improve the sensor property, the biosensor may further include a series of other functional layers. The biosensor in some embodiments usually includes the following function layers from inside to outside: an electrical conducting layer, an anti-interference layer, an enzyme layer, a regulation layer, and a biocompatibility layer. These layers may also be multi-functional.

Figure 12C:
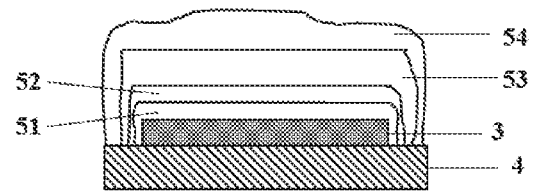

FIG. 12c is a cross-sectional view of a working electrode of a glucose biosensor according to one embodiment of the present disclosure, which illustrates various functional layers covering on the surface of the working electrode, which include an anti-interference layer (51), an enzyme layer (52), a regulation layer (53), and a biocompatibility layer (54).

The functional layers of the biosensor eliminate the possible influence of interferent on detection signals, regulate the diffusion ability of glucose and oxygen, and protect the electrodes. The biosensor provided in the present disclosure realizes the linear dependence between the detection signals and the glucose concentration in a wide detection range.

Anti-Interference Layer

The anti-interference layer is located between the enzyme layer and the electrical conducting layer. The interferent may be a kind of molecules or materials which may have electrochemical reduction or electrochemical oxidation directly or indirectly by an electron transfer reagent on the surface of the electrodes, and then produce a false signal which can interfere the analyte detection. For the glucose detection, the common interferent in vivo includes: carbamide, ascorbic acid, acetaminophen, etc.

In some embodiments, the anti-interference layer may prevent one or more kinds of interferent from diffusing into the electrolyte around the electrodes. For example, the anti-interference layer may let through the analyte (e.g., hydrogen peroxide) to be detected on the electrodes, and prevent other substances (e.g., possible interferent) from passing through. In some embodiments, the anti-interference layer may be a very thin film in order to prevent substances whose molecular weight is greater than 34D from diffusing.

In some embodiments, the anti-interference layer may be the organic polymer mentioned in the present disclosure, which may be formed by the active organosilane and a hydrophilic copolymer. In some embodiments, the hydrophilic copolymer is selected from polyethylene glycol (PEG), poly(2-hydroxyethyl)methacrylate and polylysine. In some embodiments, the amount of the hydrophilic copolymer is from 0 to 15 parts by weight (based on a condition that the amount of the active organosilane is 100 parts by weight), preferably, from 1 to 10 parts, and most preferably, from 2 to 7 parts. In some embodiments, the thickness of the anti-interference layer ranges from 0.1 to 10 micron, and preferably, from 0.5 to 5 micron.

Regulation Layer

The regulation layer is located on the enzyme layer. As described above, the regulation layer is mainly used to regulate the permeability rate of glucose and oxygen delivered to the enzyme layer. The glucose concentration (molar concentration) in blood is much higher than the oxygen concentration in blood. However, for an enzyme based biosensor that need participation of oxygen, excess oxygen is needed to ensure that the oxygen is not the limiting reagent, such that the biosensor can linearly respond to the changes of the glucose concentration rather than be affected by the oxygen partial pressure. In other words, when the oxygen concentration becomes the limiting factor, the linearity range of the glucose oxidase monitoring reaction cannot achieve the desired concentration range. When there is no semipermeable membrane on the enzyme layer to regulate the diffusion of oxygen and glucose, the upper bound of linear respond to glucose in the biosensor may only achieve 40 mg/dL. However, the upper bound of linear respond to blood glucose in clinical applications is desired to achieve 500 mg/dL.

The regulation layer is mainly used as a semipermeable membrane to regulate the permeability rate of glucose and oxygen delivered to the enzyme layer. Specifically, it makes oxygen excess to be a non-limiting factor. Compared to the biosensor without the regulation layer, the upper bound of linear respond to glucose in the biosensor with the regulation layer may achieve a higher level. In some embodiments, the proportion of the oxygen permeability rate and the glucose permeability rate of the regulation layer may achieve 200:1, so that there is enough oxygen to react with enzyme corresponding to various possible concentrations of glucose and glucose in the subcutaneous environment.

In some embodiments, the regulation layer may be the organic polymer mentioned in the present disclosure, which may be formed by the active organosilane and a hydrophilic copolymer. In some embodiments, the hydrophilic copolymer is copolymerized or grafted polyethylene glycol (PEG). Other kinds of diol are also possible, for example but not limited to propylene glycol, ester, amide, carbonic ester and polypropylene glycol. In some embodiments, the amount of the PEG or any other kind of hydrophilic copolymer is from 0 to 25 parts by weight (based on a condition that the amount of the active organosilane is 100 parts by weight), preferably, from 2 to 20 parts, and most preferably, from 5 to 15 parts. The organosilicon polymer according to embodiments of the present disclosure may increase the oxygen permeability and effectively control the glucose permeability.

In some embodiments, the thickness of the regulation layer ranges from 1 to 50 micron, preferably, ranges from 5 to 15 micron.

Biocompatibility Layer

The biocompatibility layer is located in the most outside of the electrodes in order to eliminate the rejection of the body to foreign objects, and to reduce the formation of shielding cell layers around the implanted electrodes.

In some embodiments, the biocompatibility layer may be formed by the active organosilane and a hydrophilic copolymer. In some embodiments, the hydrophilic copolymer is copolymerized or grafted polyethylene glycol (PEG). Other kinds of diol are also possible, for example but not limited to propylene glycol, ester, amide, carbonic ester and polypropylene glycol. In some embodiments, the amount of the PEG or any other kind of hydrophilic copolymer is from 5 to 100 parts by weight (based on a condition that the amount of the active organosilane is 100 parts by weight), preferably, from 10 to 80 parts, and most preferably, from 25 to 75 parts.

In some embodiments, the thickness of the biocompatibility layer ranges from 5 to 100 micron, preferably, from 10 to 30 micron.

Film Coating

The coating of the films of the biosensor can be implemented by using a commercial spin coating device with a rotation rate controlled to range from 1000 to 5000 rpm. The rotation rate is adjusted based on the stickiness of the polymer solution and the required thickness of the layer to be formed. The coating of the films of the biosensor may also use other common methods in the field, for example, dip coating, spray coating, or inkjet printing.

EXAMPLE 1

An active organosilicon polymer terminated with amino is formed by a chain extension reaction of active organosilane.

Octamethylcyclotetrasiloxane (10 g), toluene (45 ml) and PDMS terminated with amino (1.5 g, 07-0.9 meq/g) are successively added into a 100 ml three-neck flask fitted with a mechanical stirrer, a heating jacket, a thermometer, a Dean Stark water separator, a condenser, and nitrogen. The nitrogen bubbles for an hour, and then the three-neck flask is heated and kept at 140 degrees Celsius for 50 minutes. About 5 ml toluene is vaporized. After the reaction mixture is cooled to 90 degrees Celsius, 2 ml of hexane solution containing phosphazene base $P_4$-t-Bu (concentration, 1 mol/L) is added into the reaction system by an injector. Stirring and reacting for one hour, and then the system is cooled to the room temperature. The reaction mixture is washed twice by 50 ml of methanol, and then the resulting solution is removed under a reduced pressure. As such, 9.7 g of the solid organosilicon polymer terminated with amino is formed. The reaction process is shown in FIG. 7.

EXAMPLE 2

A copolymerization reaction is conducted with diisocyanate participated as a curing agent.

Dry THF (40 ml) and dehydrated 1,6-hexamethylene diisocyanate (1.34 g, 8 mmol) are successively added into a 100 ml three-neck flask fitted with a mechanical stirrer, a heating jacket, a thermometer, and a condensor. Under a condition of stirring, 1.20 g (2 mmol) of dehydrated Jeff amine 600 (polyetheramine, polyethylene glycol terminated with amino, as hydrophilic copolymer) and 7.50 g (6 mmol) of PDMS terminated with hydroxyl (HPDMS, 90000 cSt, as active organosilane) are added into the reaction mixture. The three-neck flask is heated to 50 degrees Celsius, and then 0.5 ml of THF containing 15 mg of dibutyltin bis(2-ethylhexanoate is added into the reaction mixture. After 10 minutes, the mixture is heated to 70 degrees Celsius and then the reaction is continued for a further 8 hours at 70 degrees Celsius. Then the reaction mixture is cooled to the room temperature. The viscosity of the reaction mixture increases gradually during the reaction. The cooled reaction mixture is poured into deionized water (2 L) which is quickly stirred. The precipitate is washed three times by deionized water, dried, and then further dried to constant weight under a reduced pressure at 50 degrees Celsius. As such, 8.96 g of organosilicone copolymer is formed. The reaction process is shown in FIG. 8.

EXAMPLE 3

A polymerization is conducted under the room temperature with siloxane is participated as a curing agent.

0.5 g of PDMS terminated with methyl (50 cSt, as modifier), 5 g of PDMS active organosilane terminated with hydroxyl (90-150 cSt, as active organosilane), 1 g of trimethoxy(methyl)silane (TMOMS, as curing agent) and 0.1 g of aminopropyl trimethoxysilane (APTMOS) are successively added into a 100 ml round bottom flask containing 15 ml of dry THF and 0.02 g of graphene (used as filler). After mixing, 0.1 g of tetrabutyl titanate (used as catalyst) is added and then stirring is continued for 30 minutes. The reaction mixture is spun onto a tetrafluoroethylene substrate at a rotation rate ranging from 1000 to 5000 rpm by using a commercial rotary coating device. Curing is continued for 4 hours under a relative humidity of 80%. The polymer film can be pulled off from the substrate and the thickness thereof is measured by a microcalliper. The reaction process is shown in FIG. 10.

EXAMPLE 4

A polymerization reaction is conducted in which PDMS terminated with vinyl is participated as a curing agent.

40 ml of toluene containing 10 g of PDMD terminated with hydrogen (1000 cSt, as active organosilane), and 0.25 g of Pt catalyst (concentration, 2%) are successively added into a 100 ml three-neck flask fitted with a thermometer, a mechanical stirrer, a heating jacket, a 20 ml constant pressure funnel, and a condensor. The reaction mixture is heated to 75 degrees Celsius, and 10 ml of toluene containing 2 g of PDMS terminated with vinyl (200 cSt, as a curing agent) is dropped to the flask during 3 hours. The reaction is continued for a further 6 hours, and then the heating jacket is removed to cool the reactants to the room temperature. The yellow reaction mixture is purified by column chromatography of active aluminum oxide. As such, 10.1 g of a polymer is formed. The reaction process is shown in FIG. 9.

EXAMPLE 5

A polymer film is formed with glutaraldehyde used as a curing agent.

0.2 g of PDMS terminated with aminopropyl (0.7-0.9 meq/g, as active organosilane) and 1 g of water solution of polyallylamine (Mw is about 60000, concentration 20%, as a hydrophilic copolymer) are successively added into a 50 ml round bottom flask containing 20 ml of deionized water. After mixing, the reaction mixture is casted onto a substrate of glass. Cross-linking is continued for 4 hours in an atmosphere of glutaraldehyde (as a curing agent) at 40 degrees Celsius to form a polymer film. After the cross-linking, wash the substrate with deionized water to remove the glutaraldehyde deposited on the surface. Pull the polymer film off from the substrate and measure the thickness of the polymer film by a microcalliper. The reaction process is shown in FIG. 11.

EXAMPLE 6

Polymer film are formed and tested.

Materials used herein include some organosilicon polymers with different proportions of hydrophilic copolymer, which are formed by using diisocyanate as a curing agent. The reaction process is shown in FIG. 8, and the specific formation method is illustrated in example 2. A polymer film is formed by using a spin coating process. Polymer solution (mass fraction, 7%) is spun onto a glass substrate to form the polymer film. The solvent of the solution is selected based on the specific chemical structure of the polymer. Usually, THF or DMF/$CH_2Cl_2$ (2/98%, volume ratio). The polymer film is pulled off from the substrate, and immersed in deionized water for 30 minutes. The thickness of the wet polymer film is measured by a microcalliper. The polymer film can also be formed by a casting process, including casting the solution of polymer into a filter membrane with a known thickness. In such a way, it can be assumed that the thickness of the polymer film is the same as the thickness of the filter membrane, and the polymer is fully filled in the gaps of the filter membrane.

The diffusion constant of oxygen can be measured using the follow method. Hold the polymer film between two transverse walls of a diffusion cell using two rubber washers. Two sides of the diffusion cell are filled with deionized water, while one side is saturated by nitrogen of HPLC, and the other side is saturated by air. Put oxygen electrodes which have been calibrated into the liquids in the two sides of the diffusion cell, and then seal the diffusion cell. Record, with time, the change of the oxygen concentration of the liquids in the two sides of the diffusion cell. Draw a curve representing that oxygen concentration changes with time, and calculate the diffusion constant of oxygen. When the curve is formed by fitting, the correlation coefficient ($R^2$) is required to be greater than 0.98.

The method of measuring the diffusion constant of glucose is similar to the above method. The liquids filled in the two sides of the diffusion cell are a phosphate buffer solution (PBS) whose PH value is 7.4 and a phosphate buffer solution containing glucose (concentration, 6000 mg/dL), respectively. Measure, at every fifteen minutes, the glucose concentration of the liquids in the two sides of the diffusion cell by a biochemistry analyzer. Draw a curve representing that the glucose concentration changes with time, and calculate the diffusion constant of glucose.

The method of measuring the diffusion constant of acetaminophen (as an interferent) is similar to the above method. The liquids filled in the two sides of the diffusion cell are a phosphate buffer solution and a phosphate buffer solution containing acetaminophen (concentration, 30 mg/dL), respectively. Measure, at every fifteen minutes, the acetaminophen concentration of the liquids in the two sides of the diffusion cell with reference to the absorbance of a UV spectrophotometer at 240 nm. Similarly, draw a curve representing that the acetaminophen concentration changes with time, and calculate the diffusion constant of acetaminophen.

The water absorption of the polymer film is measured using the follow method. Dry the polymer film to a constant weight at 50 degrees Celsius under vacuum. Weigh the dry polymer film. Put the dry polymer film into deionized water for 12 hours, and then remove the water on the surface of the polymer film with filter paper. And weigh the wet polymer film.

Table 1 illustrates properties of some polymer films. In table 1, the mole percent (mol. %) of Jeff amine is the mole percent of the amino in Jeff amine 600 to all the amino in Jeff amine 600 and HPDMS. In table 1, the mole percents of Jeff amine are respectively corresponding to millimoles of Jeff amine 600 and HPDMS (illustrated as A/B, A represents the millimole of Jeff amine 600 and B represents the millimole of HPDMS) as follows: 0%, 0/8; 2.5%, 0.2/7.8; 5%, 0.4/7.6; 10%, 0.8/7.2; 25%, 2/6; and 50%, 4/4. The results show that, the diffusion constants of oxygen, glucose and acetaminophen respectively have magnitudes of $10^{-5}$ cm$^2$/s, $10^{-8}$ cm$^2$/s and $10^{-8}$ cm$^2$/s. The ratio of the oxygen diffusion constant to the glucose diffusion constant ranges from 1500 to 170, which means the polymer film has good oxygen permeability and can effectively control the glucose permeability. The acetaminophen diffusion constant and the glucose diffusion constant are in the same level, which means that the polymer film has good interference immunity. The water absorption obviously increases with the increasing of the content of Jeff amine. The glucose diffusion constant and the acetaminophen diffusion constant also increase with the increasing of the content of Jeff amine, while the oxygen diffusion constant does not obviously change.

It is clear that the polymer film according to the present disclosure has good oxygen permeability and an adjustable water absorption rate, and an ability to adjust and limit the diffusion of analyte (e.g., glucose) and interferent (e.g., acetaminophen). Besides, the polymer film has necessary physical strength and good biocompatibility, thus can be used as a material for multifunctional polymer films of biosensors. For example, it can be used to form an anti-interference layer, a regulation layer, and a biocompatibility layer.

TABLE 1

(formation of each sample is the same as example 2 except the amount of Jeff amine)

| No. | Jeffamine mol. % | Water pickup % | D Oxygen *$10^{-6}$ cm$^2$/s | D Glucose *$10^{-8}$ cm$^2$/s | D Acetaminophen *$10^{-8}$ cm$^2$/s |
|---|---|---|---|---|---|
| 1 | 0 | 0.2 | 14.4 | 0.93 | 1.04 |
| 2 | 2.5 | 0.5 | 15.6 | 1.27 | 1.18 |
| 3 | 5 | 2.7 | 15.2 | 1.52 | 1.43 |
| 4 | 10 | 14.8 | 14.2 | 2.72 | 1.65 |
| 5 | 25 | 30.1 | 13.8 | 4.28 | 2.54 |
| 6 | 50 | 45.2 | 12.4 | 7.21 | 3.41 |

EXAMPLE 7

Use biosensors to detect glucose.

The polymer film in example 6 has a suitable water absorption rate, a suitable glucose diffusion constant and a suitable oxygen diffusion constant. Properties of the film (including the polymer formed in example) are further evaluated using biosensors (referring to FIG. 12, specifically referring to above content with the title for of "Biosensor") having enzyme layers and electrode layers. A commercial spin coating device is used to coat the polymer to form regulation layers of the biosensors. The rotation speed is adjusted based on required thicknesses of the coating, normally within a range from 1000 to 50000 rpm. Three biosensors without regulation layers formed by spin coating are formed as a reference group, while three biosensors with regulation layers (thickness, 5 micron) formed by coating as a test group.

Figure 13A:
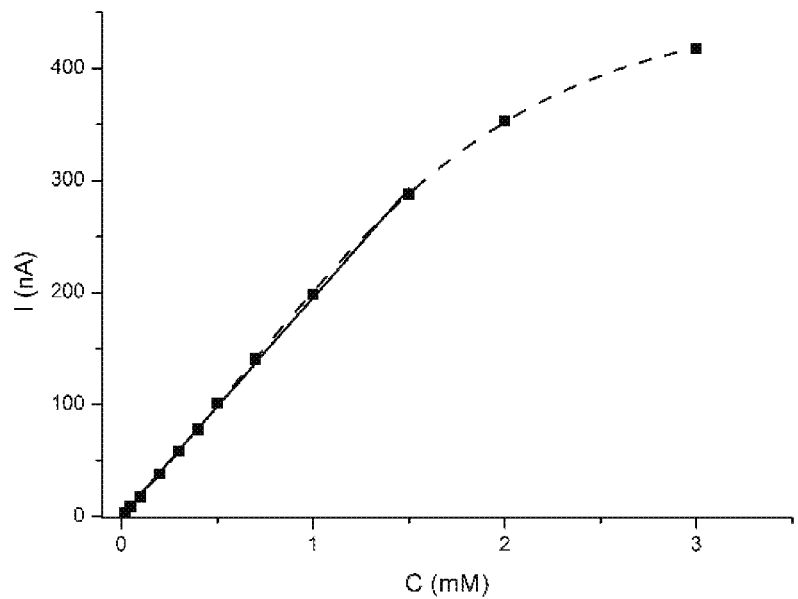
FIGS. 13a and 13b respectively illustrate relation of response current and glucose concentration.
Figure 13B:
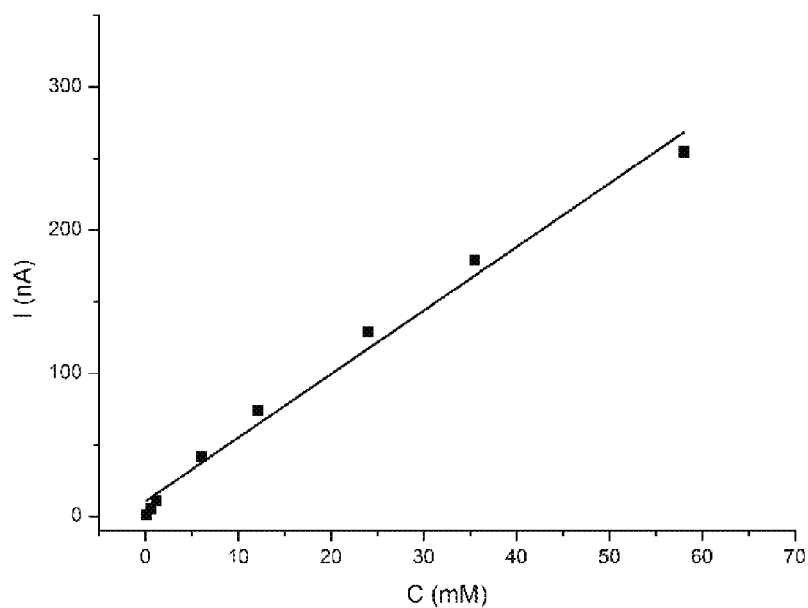

All the biosensors are equilibrated in a phosphate buffer at 37 degrees Celsius, and then are inserted into glucose solutions with different concentrations. A voltage ranging from 0.5 to 0.6V is applied between the working electrodes and reference electrodes. Record the response currents in the glucose solutions with different concentrations are recorded. Draw curves represent the relationship of the response currents and the glucose concentrations (referring to FIG. 13). And then calculate the slope rate of the curve by linear fitting. The slope rate obtained can reflect the sensitivity of the biosensor to glucose. FIG. 13a and FIG. 13b respectively illustrates test results of the reference group and the test group. 1 mM of glucose solution produces a response current of 194.6 nA and a response current of 4.44 nA in different groups, and the detection range of glucose is raised from 0.002~1.5 mM to 0.1~60 mM. The results show that the polymer film according to the present disclosure has an appropriate oxygen diffusion constant and an appropriate glucose diffusion constant, and is suitable for the regulation layer of a glucose biosensor.

EXAMPLE 8

40 ml of dry THF and 1.05 g (6.25 mmol) of dehydrated 1,6-hexamethylene diisocyanate are successively added into a 100 ml three-neck flask fitted with a mechanical stirrer, a heating jacket, a thermometer, and a condensor. During stirring, 0.15 g (0.25 mmol) of dehydrated Jeff amine 600 (polyetheramine, polyethylene glycol terminated with amino, as a hydrophilic copolymer) and 7.50 g (about 6 mmol) of PDMS terminated with hydroxyl (HPDMS, 90000 cSt, as active organosilane) are added into the reaction mixture. The flask is heated to 50 degrees Celsius, and then 0.5 ml of THF containing 15 mg of dibutyltin bis(2-ethylhexanoate) is added into the reaction mixture. Stirring is continued for a further 10 minutes, and then the reaction mixture is heated to 70 degrees Celsius. The reaction is continued for a further 8 hours at 70 degrees Celsius, and then the reaction system is cooled to the room temperature. The stickiness of the solution increases gradually during the reaction. After the cooling, the solution is poured into 2 L of deionized water which is stirred quickly. The precipitate is washed three times by deionized water, dried, and then further dried to a constant weight under a reduced pressure at 50 degrees Celsius. As such, 6.74 g of organosilicone copolymer is formed. The oxygen diffusion constant, the glucose diffusion constant and the acetaminophen diffusion constant of the organosilicone copolymer are measured (see example 6). And the sensitivity to glucose of the organosilicone copolymer is measured (see example 7). The results meet the expectations. The polymer film according to example 8 has good oxygen permeability and an adjustable water absorption rate, and an ability to adjust the permeability of glucose and the main interferent (e.g., acetaminophen). Further, it has necessary physical strength and good biocompatibility, thus can be used as a multifunctional polymer film material for biosensors, for example, used for forming an anti-interference layer, a regulation layer, and a biocompatibility layer.

EXAMPLE 9

40 ml of dry THF and 2.57 g (15.38 mmol) of dehydrated 1,6-hexamethylene diisocyanate are successively added into a 100 ml three-neck flask fitted with a mechanical stirrer, a heating jacket, a thermometer, and a condensor. During stirring, 5.63 g (9.38 mmol) of dehydrated Jeff amine 600 (polyetheramine, polyethylene glycol terminated with amino, as a hydrophilic copolymer) and 7.50 g (about 6 mmol) of PDMS terminated with hydroxyl (HPDMS, 90000 cSt, as active organosilane) are added into the reaction mixture. The flask is heated to 50 degrees Celsius, and then 0.5 ml of THF containing 15 mg of dibutyltin bis(2-ethylhexanoate) is added into the reaction mixture. Stirring is continued for a further 10 minutes, and then the reaction mixture is heated to 70 degrees Celsius. The reaction is continued for a further 8 hours at 70 degrees Celsius, and then the reaction system is cooled to the room temperature. The stickiness of the solution increases gradually during the reaction. After the cooling, the solution is poured into 2 L of deionized water which is stirred quickly. The precipitate is washed three times by deionized water, dried, and then further dried to a constant weight under a reduced pressure at 50 degrees Celsius. As such, 17.2 g of organosilicone copolymer is formed. The organosilicone copolymer is dissolved in 228.5 g of THE and then 0.75 g of PDMS terminated with methyl (50 cSt, as a modifier) and 0.38 g of fumed silica (200~300 nm, as a filler) are added. After stirring, a solution of polymer film with a mass concentration of 7% is formed. And then a film is formed by spin coating (see example 6). The oxygen diffusion constant, the glucose diffusion constant and the acetaminophen diffusion constant of the organosilicone copolymer are measured (see example 6). And the sensitivity to glucose of the organosilicone copolymer is measured (see example 7). The results meet the expectations. The polymer film according to example 9 has good oxygen permeability and an adjustable water absorption rate, and an ability to adjust the permeability of glucose and the main interferent (e.g., acetaminophen). Further, it has necessary physical strength and good biocompatibility, thus can be used as a multifunctional polymer film material for biosensors, for example, used for forming an anti-interference layer, a regulation layer, and a biocompatibility layer.

In summary, the present disclosure overcomes the various shortcomings of the current technology and has high industrial utilization value.

Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. An implantable biosensor, comprising the following functional layers:
   an anti-interference layer, an enzyme layer, a regulation layer and a biocompatibility layer,
   wherein the functional layers are produced from an organosilicon polymer, and raw materials of the organosilicon polymer comprising:
   100 parts by weight of at least one active organosilane, wherein the active organosilane comprises one or more functional groups;
   at least one curing agent;
   from 0 to 100 parts by weight of at least one hydrophilic copolymer, wherein the hydrophilic copolymer is a hydrophilic polymer with one or more functional groups; and
   from 0 to 20 parts by weight of at least one modifier; and
   from 0 to 10 parts by weight of at least one filler;
   wherein the curing agent is a chain extender with two degrees of functionality or a cross-linking agent with three or more functional groups, and the amount of the curing agent is determined as follows:
   if the curing agent is a chain extender, the number of moles of the curing agent functional groups is the sum of the number of moles of the functional groups of the active organosilane and the number of moles of the functional groups of the hydrophilic copolymer, and
   if the curing agent is a cross-linking agent, the number of moles of the curing agent functional groups is 1.05 to 1.20 times the sum of the number of moles of the functional groups of the active organosilane and the number of moles of the functional groups of the hydrophilic copolymer.

2. The implantable biosensor according to claim 1, wherein the anti-interference layer is produced from the organosilicon polymer, and raw materials of the organosilicon polymer comprise:
   100 parts by weight of the active organosilane;
   from 2 to 7 parts by weight of the hydrophilic copolymer;
   from 0 to 10 parts by weight of the modifier;
   from 0 to 5 parts by weight of the filler; and
   the curing agent, wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer; if the curing agent is a cross-linking agent, the number of moles of the curing agent is 1.10 to 1.15 times the sum of the number of moles of the functional groups of the active organosilane and the number of moles of the functional groups of the hydrophilic copolymer.

3. The implantable biosensor according to claim 2, wherein the hydrophilic copolymer is a hydrophilic polymer with one or more functional groups, and the hydrophilic copolymer is one selected from the group consisting of polyethylene glycol, poly(2-hydroxyethyl)methacrylate, polyallylamine and polylysine.

4. The implantable biosensor according to claim 1, wherein the regulation layer is produced from the organosilicon polymer, and raw materials of the organosilicon polymer comprise:
   100 parts by weight of the active organosilane;
   from 5 to 15 parts by weight of the hydrophilic copolymer;
   from 0 to 10 parts by weight of the modifier;
   from 0 to 5 parts by weight of the filler; and
   the curing agent, wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer; if the curing agent is a cross-linking agent, the number of moles of the curing agent is 1.10 to 1.15 times the sum of the number of moles of the functional groups of the active organosilane and the number of moles of the functional groups of the hydrophilic copolymer.

5. The implantable biosensor according to claim 4, wherein the hydrophilic copolymer is a hydrophilic polymer with one or more functional groups, and the hydrophilic copolymer is one selected from the group consisting of polyethylene glycol, polypropylene glycol, polyester, polyamide, polyallylamine and polycarbonate.

6. The implantable biosensor according to claim 1, wherein the biocompatibility layer is produced from the organosilicon polymer, and raw materials of the organosilicon polymer comprise:
100 parts by weight of the active organosilane;
from 25 to 75 parts by weight of the hydrophilic copolymer;
from 0 to 10 parts by weight of the modifier;
from 0 to 5 parts by weight of the filler; and
the curing agent, wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer; if the curing agent is a cross-linking agent, the number of moles of the curing agent is 1.10 to 1.15 times the sum of the number of moles of the functional groups of the active organosilane and the number of moles of the functional groups of the hydrophilic copolymer.

7. The implantable biosensor according to claim 6, wherein the hydrophilic copolymer is a hydrophilic polymer with one or more functional groups, and the hydrophilic copolymer is one selected from the group consisting of polyethylene glycol, polypropylene glycol, polyester, polyamide, polycarbonate, polyallylamine, and gelatin.

8. The implantable biosensor according to claim 1, wherein raw materials of the organosilicon polymer comprise:
100 parts by weight of the active organosilane, wherein the active organosilane comprises one or more functional groups;
from 0 to 75 parts by weight of the hydrophilic copolymer, wherein the hydrophilic copolymer is a hydrophilic polymer with one or more functional groups;
from 0 to 10 parts by weight of the modifier;
from 0 to 5 parts by weight of the filler; and
the curing agent, wherein the amount of the curing agent is determined as follows: if the curing agent is a chain extender, the number of moles of the curing agent is the sum of the number of moles of the functional groups of the active organosilane and the number of moles of the functional groups of the hydrophilic copolymer; if the curing agent is a cross-linking agent, the number of moles of the curing agent is 1.10 to 1.15 times the sum of the number of moles of the functional groups of the active organosilane and the number of moles of the functional groups of the hydrophilic copolymer;
wherein a main part of the active organosilane is polydimethylsiloxane, a part of methyl groups of the polydimethylsiloxane is substituted by monovalent organic groups with a substitution rate of less than or equal to 30%, and the monovalent organic group is selected from the group consisting of hydrogen, aliphatic chain, aromatic chain, and ether chain; and
the functional groups of the active organosilane are one or more of the functional groups selected from the group comprising of hydroxyl group, amino group, carboxyl group, hydrogen group, alkoxyl group, phenoxyl group, vinyl group, acyl group, oxime group, cyano group, allyl group, epoxy group, and isocyano group.

9. The implantable biosensor according to claim 8, wherein the hydroxyl group is hydroxypropyl, the amino group is ethylamino or aminopropyl, the carboxyl group is butyric acid group, and the alkoxyl group is methoxyl or ethoxyl.

10. The implantable biosensor according to claim 8, wherein the one or more functional groups of the hydrophilic copolymer are terminal functional groups or pendant functional groups, and the one or more functional groups of the hydrophilic copolymer are hydroxyl groups or amino groups.

11. The implantable biosensor according to claim 10, wherein the hydrophilic copolymer is polyether, polyester, polycarbonate, polyamide, or another polymer with pendant hydroxyl or pendant amino.

12. The implantable biosensor according to claim 11, wherein the hydrophilic copolymer is selected from the group consisting of polyethylene glycol terminated with amino, polypropylene glycol terminated with amino, poly (2-hydroxyethyl)methacrylate, polyallylamine, polylysine, polypeptides and proteins including gelatin, and any combination thereof.

13. The implantable biosensor according to claim 8, wherein the cross-linking agent is a silicone cross-linking agent that can participate in a condensation reaction, wherein the small molecule removed in the condensation reaction can be water, methanol, ethanol, acetone or acetic acid, and the chain extender is a silicone chain extender, diisocyanate, or glutaraldehyde.

14. The implantable biosensor according to claim 13, wherein the silicane chain extender has terminal vinyl which can react with PDMS terminated with hydrogen, and the diisocyanate is selected from the group consisting of 1,6-hexamethylene diisocyanate, diisocyanate with the structure of isophorone, 1,3-phenyl diisocyanate, and other aromatic diisocyanate.

15. The implantable biosensor according to claim 8, wherein the modifier is inactive silicane or active small molecule.

16. The implantable biosensor according to claim 15, wherein the modifier is selected from the group consisting of short chain PDMS terminated with methyl, aliphatic diol, aliphatic triol, aliphatic diamine, aromatic diamine, and any combination thereof.

17. The implantable biosensor according to claim 8, wherein the filler is selected from the group consisting of fumed silica, alumina, carbon black, titanium dioxide, glass fiber, carbon fiber, diatomaceous earth, synthetic fiber, and nanoparticles.

* * * * *